US010987822B2

(12) United States Patent
Ursella et al.

(10) Patent No.: US 10,987,822 B2
(45) Date of Patent: Apr. 27, 2021

(54) METHOD FOR ESTABLISHING A POSTERIORI A MATCH BETWEEN A PIECE OF WOOD AND A LOG FROM WHICH THE PIECE OF WOOD HAS BEEN OBTAINED

(71) Applicant: MICROTEC S.R.L., Bressanone (IT)

(72) Inventors: Enrico Ursella, Mestre (IT); Enrico Vicario, Martellago (IT); Martin Bacher, Pfalzen (IT)

(73) Assignee: MICROTEC S.R.L., Bressanone (IT)

( * ) Notice: Subject to any disclaimer, the term of this patent is extended or adjusted under 35 U.S.C. 154(b) by 244 days.

(21) Appl. No.: 16/297,107

(22) Filed: Mar. 8, 2019

(65) Prior Publication Data

US 2019/0283266 A1 Sep. 19, 2019

(30) Foreign Application Priority Data

Mar. 13, 2018 (IT) .................. 102018000003506

(51) Int. Cl.
| | | |
|---|---|---|
| *B27B 1/00* | (2006.01) | |
| *G06T 7/60* | (2017.01) | |
| *G06K 9/62* | (2006.01) | |
| *G06T 7/70* | (2017.01) | |
| *G06T 7/00* | (2017.01) | |
| *G01N 33/46* | (2006.01) | |
| *G01N 23/046* | (2018.01) | |
| *G01N 29/06* | (2006.01) | |
| *G01N 24/08* | (2006.01) | |
| *B27D 1/00* | (2006.01) | |
| *G06F 16/23* | (2019.01) | |

(52) U.S. Cl.
CPC ............. *B27B 1/007* (2013.01); *B27B 1/00* (2013.01); *B27D 1/00* (2013.01); *G01N 23/046* (2013.01); *G01N 24/085* (2013.01); *G01N 29/0672* (2013.01); *G01N 33/46* (2013.01); *G06K 9/6201* (2013.01); *G06T 7/001* (2013.01); *G06T 7/60* (2013.01); *G06T 7/70* (2017.01); *G01N 2223/619* (2013.01); *G01N 2291/0238* (2013.01); *G06F 16/23* (2019.01); *G06T 2207/10024* (2013.01); *G06T 2207/10028* (2013.01); *G06T 2207/10048* (2013.01); *G06T 2207/10072* (2013.01); *G06T 2207/10116* (2013.01); *G06T 2207/30161* (2013.01)

(58) Field of Classification Search
CPC .. B27B 1/00; B27B 1/007; B27D 1/00; G01N 2223/619; G01N 2291/0238; G01N 23/046; G01N 24/085; G01N 29/0672; G01N 33/46; G06F 16/23; G06K 9/6201; G06T 2207/10024; G06T 2207/10028; G06T 2207/10048; G06T 2207/10072; G06T 2207/10116; G06T 2207/30161; G06T 7/001; G06T 7/60; G06T 7/70
See application file for complete search history.

(56) References Cited

U.S. PATENT DOCUMENTS

| | | | |
|---|---|---|---|
| 4,879,752 A | 11/1989 | Aune et al. | |
| 5,257,101 A | 10/1993 | Lee | |
| 6,029,522 A | 2/2000 | Schafer et al. | |
| 2005/0161118 A1 | 7/2005 | Carman et al. | |
| 2006/0048852 A1* | 3/2006 | McIntosh ................. | B27M 1/02 144/380 |
| 2006/0260718 A1* | 11/2006 | Neglay ................... | B27B 1/007 144/356 |
| 2006/0289086 A1* | 12/2006 | Rinfret .................. | B27L 11/007 144/357 |
| 2007/0119518 A1 | 5/2007 | Carman et al. | |

(Continued)

FOREIGN PATENT DOCUMENTS

FR 2797975 3/2001

OTHER PUBLICATIONS

Bhandarkar, S.M., et al., "Automated Planning and Optimization of Lumber Production Using Machine Vision and Computed Tomography", IEEE Transactions on Automation Science and Engineering, IEEE Service Center, New York, New York, US, vol. 5, No. 4, Oct. 1, 2008, pp. 677-695, XP011331796.

*Primary Examiner* — Bobbak Safaipour
(74) *Attorney, Agent, or Firm* — Pearne & Gordon LLP

(57) ABSTRACT

A method for establishing a posteriori a match between a piece of wood and a log from which the piece of wood has been obtained, comprising the following operating steps of performing a tomographic scan of the wooden log, of calculating or selecting a log cutting pattern, of defining, starting with the tomographic information available, one or more virtual individualising characteristics which are linked to the distribution and/or size of physical characteristics of the log inside and/or on the surface of the self-same virtual piece of wood, of saving them in a database, together with information about the identity of the log, of dividing the log into real pieces of wood according to the cutting pattern, of acquiring real information about the distribution and/or size of physical characteristics of the log inside and/or on the surface of a real piece of wood and of defining corresponding real individualising characteristics to be compared with virtual individualising characteristics saved and of identifying an origin of the real piece of wood based on the information about the identity of the log which is saved together with the virtual individualising characteristics which match the real individualising characteristics.

20 Claims, No Drawings

(56) References Cited

U.S. PATENT DOCUMENTS

| | | | |
|---|---|---|---|
| 2010/0161096 A1* | 6/2010 | Giudiceandrea | B27B 1/00 700/98 |
| 2010/0228380 A1* | 9/2010 | Giudiceandrea | B27B 1/00 700/118 |
| 2011/0069811 A1* | 3/2011 | Giudiceandrea | G06T 7/0004 378/21 |
| 2012/0022829 A1* | 1/2012 | Giudiceandrea | G01N 23/046 702/167 |
| 2012/0170055 A1* | 7/2012 | Giudiceandrea | G01N 21/23 356/614 |
| 2013/0173179 A1 | 7/2013 | Giovanini et al. | |
| 2014/0244023 A1* | 8/2014 | Saastamo | B26D 5/007 700/171 |
| 2018/0313809 A1* | 11/2018 | Ursella | G01N 23/046 |

* cited by examiner

METHOD FOR ESTABLISHING A POSTERIORI A MATCH BETWEEN A PIECE OF WOOD AND A LOG FROM WHICH THE PIECE OF WOOD HAS BEEN OBTAINED

This invention relates to a method for establishing a posteriori a match between a piece of wood and a log from which the piece of wood has been obtained, as well as some particularly innovative parts and uses of that method.

In particular, this invention relates to a method which allows the tracing of the log from which a piece of wood originated, and if necessary the retrieving of previously saved information about the piece of wood (even for the purpose of being able to repeatedly validate the operation of the various apparatuses of the plant). In some applications the method according to this invention also allows definition of the relative position of the wooden board inside the log.

It should be noticed that in the context of this invention the definition "piece of wood" means any product obtainable by cutting a log. The most common types of piece of wood are boards and thin sheets.

In general, the ability to know the log of origin of a piece of wood allows various advantages.

First, it allows complete traceability both within the sawmill and relative to everything preceding and following the working in the sawmill, that is to say, the forest-to-sawmill leg and the sawmill-to-end product leg. Knowing this information on one hand allows a stronger guarantee to be given to the end customer, and on the other hand allows industrial operators to understand the best zones or production techniques in the forest.

Second, as already indicated, knowing the log of origin of a piece of wood also allows an understanding of whether or not the whole plant is operating as it should do. In particular, modern plants carry out log cutting using optimised cutting patterns designed based on the characteristics of each log and of each wooden board to be obtained. Therefore, knowing the log of origin of a piece of wood, and if necessary the relative position of that piece of wood inside the log, makes it possible to check if the products forecast to be obtained with the optimisation have actually been obtained, or if there have been problems in the line (incorrect cuts, defects not seen during the optimisation step, ruined material, etc.).

Furthermore, if in the plant a tomographic scan is performed on each log, then knowing the log of origin of a piece of wood and the relative position of that wooden board inside the log, makes available the internal tomographic data of the piece of wood without the need to carry out a further tomographic scan on each individual piece of wood. That also means being able to easily understand if the wood of which each board is composed is heartwood, sapwood or medulla of the starting log.

In prior art plants there are no solutions capable of guaranteeing the results indicated above.

In particular, whilst over time various solutions have been suggested for tracing a board from the moment when it is cut onwards, as well as establishing a posteriori a match between a board and a log for particular types of wood characterised by a predetermined growth regularity, no solutions have ever been suggested for establishing a posteriori a match between a generic piece of wood and a particular log which are usable with any type of wood, nor for establishing a match between a piece of wood and a specific inner portion of a log.

The board traceability solutions adopted up to now can be separated into invasive solutions (in which the identifying information is applied, written or carved on the board) and non-invasive solutions, in which the board is gradually recognised at various stations depending on its recognisable aesthetic characteristics (which form a kind of board "fingerprint"). However, they all involve starting the board tracing after the moment when the board has actually been produced.

In this context, the technical purpose forming the basis of this invention is to provide a method for establishing a posteriori a match between a piece of wood and a log which is usable with any type of wood.

In particular, the technical purpose of this invention is to provide a method for establishing a posteriori a match between a piece of wood and a log from which the piece of wood has been obtained, of the non-invasive type and which can be implemented completely autonomously by various apparatuses of a wood working plant.

It is also the technical purpose of this invention to provide a method for establishing a posteriori a match between a piece of wood and an inner portion of a log from which the piece of wood has been obtained.

It is also the technical purpose of this invention to provide a method for validating the operation of one or more apparatuses of a plant, which use the method according to this invention to establish a posteriori a match between a piece of wood and a log from which the piece of wood has been obtained.

The technical purpose specified and the aims indicated are substantially achieved by a method for establishing a posteriori a match between a piece of wood and a log from which the piece of wood has been obtained as described in the appended claims.

This invention also relates to a method for deciding a cutting pattern to be used for dividing a wooden log into pieces of wood, which is based on several aspects of the method for establishing a posteriori a match between a piece of wood and a log from which the piece of wood has been obtained. Further features and the advantages of this invention are more apparent in the detailed description below, with reference to several preferred, non-limiting embodiments of a method for establishing a posteriori a match between a piece of wood and a log from which the piece of wood has been obtained.

It should be noticed that all of the steps described in the context of this description must be understood to be steps preferably performed by devices capable of performing them autonomously, not as steps to be performed manually by operators.

The method according to this invention initially comprises an initial step of taking a wooden log. In this context the term "taking" simply refers to the fact that a wooden log has been sent for subsequent steps. Whether the log is selected randomly, or based on any special criterion, or simply corresponds to gradually taking the various logs which are fed to the plant, is completely irrelevant.

It should also be noticed that all of the steps described below as being performed on a log will generally be repeated for a plurality of logs involved or, preferably, for all of the logs which are worked on in the plant. In fact, as will become clearer in the description below, that allows the creation of a database for storing the data of all of the pieces of wood produced by the plant and which therefore allows a posteriori identification of each individual piece of wood and if necessary, its matching to a specific portion of a log.

The log taken then undergoes a scanning step, wherein a computerised tomographic scan of the log is performed using a tomographic scanner; the data obtained in this way is advantageously saved in a database, together with data about the origin of the log (what type of wood, forest of origin, zone of the forest, etc.). It should be noticed that in the context of this invention the definition of "tomographic scan" must be given its broadest meaning (therefore, it includes tomographic scans carried out using X-rays, as well as those carried out with other techniques such as ultrasound, magnetic resonance, etc.).

Then, in the known way, the method comprises a computer carrying out a step of choosing a cutting pattern, during which a cutting pattern for the log is calculated or selected. Generally, in the case of calculation of the cutting pattern the principle followed is that of attempting to maximise the economic value obtainable from the pieces of wood (calculation algorithms of this type are in themselves known and already widely used in the sector). In particular, the cutting pattern may advantageously be calculated based on the information collected during the scanning step (if necessary with the addition of other information available about the log or with economic information saved in the computer).

Alternatively, however the cutting pattern may be chosen in other ways (for example, it may be the same for all logs of a certain species, or at least for all logs with a diameter within a predetermined range of values).

Once defined, the cutting pattern may comprise information about only a subsequent division of the log into pieces of wood, or about a method for preliminary outer working of the log, and about a subsequent division of the preliminarily worked log into pieces of wood (the nature of the preliminary working is indicated below).

Hereinafter in the description the concepts of "real" and "virtual" will be introduced with reference both to the pieces of wood and their characteristics. It should be noticed that the term "real" refers to pieces of wood which are actually obtained and therefore which can be used and inspected. In contrast, the term "virtual" refers to computerised models of the pieces of wood which only exist in a computer.

Once the cutting pattern has been defined, the method according to this invention comprises a characterising step, during which for each piece of wood intended to be obtained with the cutting pattern, one or more virtual individualising characteristics are defined. Those individualising characteristics are identified without the piece of wood having had to be actually cut; in fact they are obtained exclusively starting from the tomographic information available.

In particular, the virtual individualising characteristics are advantageously linked to the distribution and/or size of physical of physical characteristics of the log inside and/or on the surface of each piece of wood. For example, the virtual individualising characteristics may be obtained by considering the shape, size and reciprocal position of knots of the log at either a two-dimensional level (for example, on one or more surfaces of the virtual piece of wood) or at a three-dimensional level (for example, in the whole volume of the piece of wood). Additionally or alternatively, the virtual individualising characteristics may also correspond to a two-dimensional distribution of grains on one or more faces of the virtual piece of wood, or the trend of the direction of the fibre of the wood on one or more faces of the virtual piece of wood.

The virtual individualising characteristics may also be translated in the form of virtual images which one could expect to obtain by photographing the surface of the piece of wood or by radiographing the piece of wood. In fact, those virtual images may be created by applying the cutting pattern to the tomographic model of the log so as to obtain a virtual model of the piece of wood and, on that virtual model, simulating taking a photograph rather than radiographing it, etc.

In one embodiment of the method according to this invention, in which the virtual individualising characteristics are obtained by considering the knots of the log at one or more surfaces of the piece of wood, each virtual individualising characteristic is defined by the position of a knot on the surface of the piece of wood, minus a predetermined margin of error, calculated depending on the orientation of the knot relative to the surface. During definition of the virtual individualising characteristics, the position of each knot on the surfaces of the piece of wood is defined by considering the virtual intersection of the surfaces themselves (for example, planes in the case of boards) with the three-dimensional knots identified with the tomographic scan. The position may advantageously be defined either with reference to a central point of the intersection, or with reference to the whole area of the intersection (therefore also considering its extension).

In contrast, advantageously the margin of error is calculated by considering the angle of intersection of the three-dimensional knot with the board, that is to say, the angle which a central axis of the knot forms with the virtual cutting surface. In fact, the greater the inclination of the knot is relative to the surface, the greater the influence on the detectable position may be, of small errors of the real cutting plane relative to the virtual cutting plane. It should be noticed that, in this context, the minimum inclination is null and is present if the central axis of the knot is perpendicular to the surface of the virtual piece of wood. It is easy to see how the greater the inclination is, the greater the deviation of the real position of the knot on the surface may be relative to the virtual position, with respect to the same error in positioning of the cut.

Therefore, the reason why each position of a knot on the virtual surface of a virtual piece of wood is also associated with a predetermined margin of error of the type described above, is to guarantee the recognisability of the piece of wood even if the cutting precision is not high.

The characterising step is also advantageously performed by means of a computer, which may or may not be the same one used for the step of choosing the cutting pattern. Moreover, the same computer also preferably performs the subsequent saving step, during which the virtual individualising characteristics identified for each virtual piece of wood, are saved in a database, together with information about the identity of the log (if necessary also together with tomographic information—alternatively the latter may be saved only once for the whole log). However, advantageously, for each virtual piece of wood, together with the information about the identity of the log, information is also saved about the position of the piece of wood in the log, and/or information about the dimensions of the virtual piece of wood (such as the thickness, the width, the length and the shape of the cross-section).

At this point the method may comprise carrying out a preliminary working step, usually intended to render the log more suitable for the subsequent step of cutting into pieces of wood.

The preliminary working step may consist of squaring, of making one or more longitudinal cuts so as to create one or more flat faces which can subsequently be used as a reference, or of carrying out simple cleaning using a chipper.

It should be noticed that it is also possible that any real pieces of wood cut during the preliminary working step correspond to virtual pieces of wood which were to be obtained with the cutting pattern foreseen.

All of the preliminary working operations which involve making at least one cut may advantageously be performed by means of a special apparatus (such as a squaring machine) which receives as input the information about the cutting pattern from the computer which processed it.

As is known, the operation for squaring a log may be the most complex to precisely perform mechanically, because one must start with an unworked log and produce a kind of beam, that is to say, a piece of wood in which on four sides consisting of two parallel opposite pairs, milling or cutting has been used to remove a part of the wood in such a way as to have a smooth/uniform surface (usually flat on the top and bottom, but not necessarily on the sides). After this step the mechanical working operations are much more precise because the machines can use the squared surfaces as a reference. In contrast, during the squaring step there are many degrees of freedom: rotation about all of the axes, vertical and lateral movement, curved cutting. The latter degree of freedom makes it possible to ensure that the smooth surfaces created on the sides form a vertical segment (perpendicular to the upper and lower surfaces) if sectioned according to a vertical plane perpendicular to the longitudinal line of the log, but may form a curved line if sectioned according to a horizontal plane parallel to the longitudinal line of the log. However, there may be similar problems when carrying out all of the other types of surface working operations, especially those which involve making at least one cut.

As described in more detail below, all of these degrees of freedom are advantageously set based on the cutting pattern previously calculated, but sometimes may not be performed precisely. In the most complete embodiment in which there is preliminary working, the method according to this invention may therefore comprise three further additional steps, a checking step, a comparing step and a correcting step for correcting the cutting pattern (although in simpler embodiments these steps may even be omitted).

During the checking step, after having undergone preliminary working, the log is measured or analysed for the purpose of defining characteristics comparable with those obtainable from the cutting pattern applied to the log tomographic data.

For example, that step may be performed with a scanner capable of detecting physical characteristics of the surface of the log (by means of colour images, NIR—Near Infra-red Reflectance analysis, or scatter laser based on the trochoidal effect—in itself known and therefore not described in detail herein) or an apparatus capable of capturing an image of its density using X-rays. The outer shape of the preliminarily worked log may also be measured.

Advantageously, the same computer may then perform the comparing step, during which the results of the checking step are compared with similar results obtainable by applying the cutting pattern to the tomographic image of the log (that is to say, obtaining a virtual preliminarily worked log), with the aim of verifying whether or not the log has been preliminarily worked as foreseen in the cutting pattern.

The correcting step for correcting the cutting pattern must be carried out if the result of the comparing step indicates that the log has been preliminarily worked in a way that is different to what was foreseen, and during the correcting step the cutting pattern previously defined is modified (recalculated) in order to adapt it to the log as it was really preliminarily worked. Depending on requirements, the cutting pattern can be modified so as to correct any deviations between the real and virtual worked log (for example, by modifying the width or height in predetermined zones, or taking into account that the real cut is rotated through a predetermined angle relative to the virtual one initially foreseen), or even for identifying a completely different cutting pattern which better optimises the economic value obtainable from the pieces of wood starting from the preliminarily worked squared log.

Returning to the main steps of the method according to this invention, once the log, if necessary, has undergone preliminary working and the cutting pattern has been updated, there is a cutting step, during which the log (intact or preliminarily worked) is divided into real pieces of wood as foreseen in the cutting pattern. Generally, during the cutting step the pieces of wood are generated with a length corresponding to that of the whole log (like the virtual ones foreseen in the cutting pattern); however it is possible that, during a subsequent dividing step, at least one real piece of wood obtained from the cutting step may also be shortened or divided into pieces either longitudinally or transversally (this is possible even if not explicitly foreseen in the cutting pattern), producing further real pieces of wood.

In some preferred embodiments, before the step of dividing at least one real piece of wood into further real pieces of wood, the method according to this invention comprises a step of choosing a secondary cutting pattern for each real piece of wood to be divided. The choice of the secondary cutting pattern may be made using the same methods indicated above for the overall log cutting pattern, and the secondary cutting pattern will comprise information with reference to a subsequent division of the at least one real piece of wood into further virtual pieces of wood.

Moreover, advantageously, before the step of dividing the at least one real piece of wood into further real pieces of wood, and after the step of choosing a secondary cutting pattern, there may also be a further characterising step. During the further characterising step, for each further virtual piece of wood intended to be obtained from the at least one real piece of wood to be divided, and starting with the tomographic information available, one or more further virtual individualising characteristics are defined which are linked to the distribution and/or size of physical characteristics of the log inside and/or on the surface of the further virtual piece of wood.

Consequently, during the saving step the virtual individualising characteristics of each further virtual piece of wood are also saved in the database similarly to what occurs for the other virtual pieces of wood. If necessary or appropriate, the saving step may be carried out at multiple successive moments as the information about the virtual individualising characteristics gradually becomes available.

Hereinafter when reference is made to real pieces of wood, it generically means both those obtained after the cutting step and those obtained after the dividing step.

All of the real pieces of wood obtained are then generally sent along a line where they can undergo further working or checks, until they finally reach a storage zone.

According to this invention, both during those further processing operations or checks, and during the subsequent storage, at any time it is possible to carry out a selecting step, during which a real piece of wood is selected whose origin is to be traced.

For that purpose, the selected real piece of wood undergoes an analysing step, a search step and an identifying step.

During the analysing step, first, real information about the distribution and/or size of physical characteristics of the log inside and/or on the surface of the real piece of wood is acquired. Exactly as described for the preliminarily worked squared log, that information may be obtained by using a scanner capable of defining the physical characteristics of the surface of the log (by means of colour images, NIR analysis, or scatter laser based on the trochoidal effect) or an apparatus capable of capturing an image of its density using X-rays.

Also during the analysing step, based on the real information acquired from the real piece of wood, corresponding real individualising characteristics of the piece of wood are defined according to the same criteria already indicated for the virtual individualising characteristics; therefore, even the real individualising characteristics will advantageously be linked to the distribution and/or size of knots inside and/or on the surface of the real piece of wood and for example may be obtained by considering the shape, size and reciprocal position of the knots of the log both at a two-dimensional level (on one or more surfaces of the real piece of wood) or at a three-dimensional level, or may correspond to a two-dimensional distribution of grains on one or more faces of the real piece of wood, or the trend of the direction of the fibre of the wood on one or more faces of the real piece of wood. Therefore, for each real piece of wood, as previously for each virtual piece of wood, a group of individualising characteristics will be created.

During the subsequent search step the real individualising characteristics of the real piece of wood are compared with the virtual individualising characteristics saved in the database, with the aim of attempting to identify a match between them. In particular, there will be a match when the comparison between the real individualising characteristics and the virtual individualising characteristics highlights a deviation which is less than a predetermined tolerance; alternatively, it there is the certainty that the piece of wood is present in the database, it is also possible to in any case choose the best match even if the deviation were greater than the predetermined tolerance.

It should be noticed that the search step may also be carried out if the real pieces of wood are smaller than the virtual pieces of wood (not vice versa) since in that case the real individualising characteristics correspond to a sub-set or sub-group of virtual individualising characteristics.

Therefore, in this case, during the search step, the real individualising characteristics of the real piece of wood are also compared with sub-groups of virtual individualising characteristics saved in the database, in order to identify said match.

Depending on the embodiments, various solutions may be adopted to facilitate carrying out the search step. In particular, to minimise the number of comparisons to be carried out, the comparisons may only be carried out between a real piece of wood and virtual pieces of wood which have compatible dimensions, that is to say, dimensions which are not smaller.

According to another option, each real piece of wood may be compared first with the whole virtual pieces of wood, and only afterwards, if a match is not identified, only with parts of the virtual pieces of wood (this is because only a few real pieces of wood are usually obtained by means of a subsequent dividing step).

According to another particularly preferred embodiment of the method, when the search step involves a comparison between real pieces of wood and parts of virtual pieces of wood, the real individualising characteristics of the real piece of wood are compared with sub-groups of virtual individualising characteristics saved in the database only for virtual pieces of wood which have the same thickness as the real piece of wood and the other dimensions greater than or equal to those of the real piece of wood.

In the case of the example indicated above in which each virtual individualising characteristic is defined by the position of a knot on the surface of the piece of wood, minus a predetermined margin of error calculated depending on the orientation of the knot relative to the surface, during the analysing step, for each piece of wood the knots present on the outer surface are identified and, for each of them, the position is identified (for example using the same system of coordinates used in the characterising step, as well as the same position identification criterion—central point rather than whole area).

Therefore, for each knot identified on the real piece of wood, during the search step a search is performed, in each virtual piece of wood, for the knot with the most similar coordinates, and the geometric distance between the two is weighed depending on the predetermined margin of error; that implies that the geometric distance being equal, during the analysing step greater importance is assigned to knots whose predetermined margin of error was lower (therefore, knots perpendicular to the surface will be more important than inclined knots). Therefore, for each piece of wood all of its knots are compared with those of each virtual piece of wood, so as to calculate a weighed distance for each knot and to add together the weighed distances.

The sum of all of the weighed distances is used as a similarity index between the pieces of wood for identifying the best match; depending on the method of weighing the distance, the best match may be either that for which the sum of the weighed distances is at the maximum or that for which it is at the minimum. Therefore, it should be considered that the real piece of wood corresponds to the virtual piece of wood for which the best match is found.

In one embodiment, the margin of error is equal to the inverse of the tangent of the angle formed by the central axis of the knot with the virtual cutting surface (if the angle is 0°, that is to say, if the central axis is perpendicular to the virtual cutting surface, even small errors have a very big weight, whilst if the angle is large, relatively large errors may have a very small weight).

In other embodiments, the margin of error may be calculated as the sum of two error components (which are calculated for example as indicated above) which make it possible to take into account in a different way any errors in the lying plane of the central axis of the knot which is perpendicular to the cutting surface, and those perpendicular to that plane. For example, the error may therefore be represented by a vector. Returning to the final main step of the method, during the identifying step, the origin of the piece of wood is identified using the information about the identity of the log which is saved in the database together with the virtual individualising characteristics for which a match was found to the real individualising characteristics of the piece of wood. In this step, if the information is available in the database, it is also possible to define the position that the piece of wood occupied in the log. This step is also performed by means of a computer.

At the same time, during the identifying step it is also possible that the same computer retrieves information about the tomographic scan of the piece of wood in question; as already indicated, that information may already be saved ready in the database together with the corresponding virtual individualising characteristics or may be obtained by extrapolating it from the overall log information.

It should be noticed that although this invention relates first to the method for establishing a posteriori a match between a piece of wood and a log from which the piece of wood has been obtained, in its most complete version described above it comprises a further specific innovative aspect worthy of independent protection. This is the set of operating steps relating to modification/adaptation of the cutting pattern which are performed after the log has undergone the preliminary working step, operating steps without precedents in the prior art systems and methods for optimising the cutting pattern.

Moreover, as already indicated, this invention also relates to use of the method for establishing a posteriori a match between a piece of wood and a log from which the piece of wood has been obtained, within a method for validating and checking the operation of the plant. In fact, thanks to this invention, the plant can be capable of performing a sort of self-diagnosis so as to verify that all of the various apparatuses used operate in the best way.

For that purpose, once the match has been identified between the real piece of wood and the log from which the piece of wood has been obtained, a comparison step is performed, during which the real piece of wood obtained is compared with the corresponding virtual piece of wood foreseen in the cutting pattern. That comparison may relate to various aspects: the dimensions of the piece of wood, the distribution of the physical characteristics in the piece of wood, the mechanical properties, the presence of defects, if any (whether or not these were foreseen at the time of choosing the cutting pattern), etc.

From an operating viewpoint the comparison step is performed by a computer as regards the actual comparison, whilst it may involve the use of special apparatuses for obtaining the information to be compared (scanners, video cameras, radiographic devices, devices for estimating the modulus of elasticity, etc.).

The results of the comparison step are then used in a validating step, during which the operation of the various apparatuses used while performing the method described above is validated or not.

In particular, the operation is considered validated only when the one or more reference characteristics of the real piece of wood deviate from those of the virtual piece of wood by less than a predetermined threshold value.

In contrast, if the deviation is greater than that threshold value, the operation of the plant cannot be validated and the operator knows that the plant requires maintenance.

For example, following the comparison and validation steps the following problems may emerge:
- a malfunction of the tomographic scanner when following the checks it is noticed that the tomographic data does not highlight defects or characteristics of the wood;
- a malfunction of the computer responsible for optimising the cutting pattern (or in any case unsuitability of the algorithm used), if it is noticed that the real pieces of wood actually obtained have defects which make their economic value lower than expected;
- poor operation of the mechanical parts responsible for moving the log or the blades during the various cutting steps, where the cutting actually carried out does not match that foreseen.

This invention brings important advantages.

First, thanks to this invention it has been possible to provide a method for establishing a posteriori a match between a piece of wood and a log from which the piece of wood has been obtained, which can be used with any type of wood.

Second, it is a method of the non-invasive type and which can be implemented completely autonomously by various apparatuses of a wood working plant.

Furthermore, thanks to this invention it has been possible to develop a method for validating the operation of one or more apparatuses of a plant.

Finally, it should be noticed that this invention is relatively easy to produce and that even the cost linked to implementing the invention is not very high. The invention described above may be modified and adapted in several ways without thereby departing from the scope of the inventive concept.

All details may be substituted with other technically equivalent elements and the materials used, as well as the shapes and dimensions of the various components, may vary according to requirements.

The invention claimed is:

1. A method for establishing a posteriori a match between a piece of wood and a log from which the piece of wood has been obtained, comprising the following operating steps:
    an initial step of taking a wooden log;
    a scanning step, wherein a tomographic scan of the wooden log is performed;
    a step of choosing a cutting pattern, during which a cutting pattern for the log is calculated or selected, the cutting pattern comprising information with reference to a subsequent division of the log into pieces of wood;
    a characterising step, during which for each virtual piece of wood intended to be obtained with the cutting pattern, and starting with the tomographic information available, one or more virtual individualising characteristics are defined which are linked to the distribution and/or size of physical characteristics of the log inside and/or on the surface of the self-same virtual piece of wood;
    a saving step, during which those virtual individualising characteristics of each virtual piece of wood are saved in a database, together with information about the identity of the log;
    a cutting step, during which the log is divided into real pieces of wood according to what is foreseen in the cutting pattern;
    a selecting step, during which a real piece of wood obtained from the cutting step is selected;
    an analysing step, during which real information about the distribution and/or size of physical characteristics of the log inside and/or on the surface of the real piece of wood is acquired and, based on that real information, corresponding real individualising characteristics of the real piece of wood are defined;
    a search step, during which the real individualising characteristics of the real piece of wood are compared with the virtual individualising characteristics saved in the database for virtual pieces of wood, in order to identify a match;
    and an identifying step, during which an origin of the real piece of wood is identified based on the information about the identity of the log which is saved in the database together with the virtual individualising characteristics of a virtual piece of wood which match the real individualising characteristics of the real piece of wood.

2. The method according to claim 1, wherein during the saving step the virtual individualising characteristics are saved in the database together with both information about the identity of the log and about the position of the virtual piece of wood in the log, and wherein during the identifying step the origin of the real piece of wood is identified based on the information about the identity of the log and the position of the virtual piece of wood in the log which is saved in the database together with the virtual individualising characteristics for which a match was found to the real individualising characteristics of the piece of wood.

3. The method according to claim 2, wherein the virtual individualising information defined during the characterising step corresponds to:
- a two-dimensional or three-dimensional distribution of knots on one or more faces of the virtual piece of wood, and/or inside the virtual piece of wood; and/or
- a two-dimensional distribution of grains on one or more faces of the virtual piece of wood; and/or
- a trend of the direction of the fibre of the wood on one or more faces of the virtual piece of wood.

4. The method according to claim 2, wherein the real information acquired during the analysing step corresponds to an arrangement of physical characteristics of the log on an outer surface of the real piece of wood and is obtained either by acquiring an image of an outer surface of the real piece of wood, in colour in the visible and/or infra-red spectra, and/or by projecting one or more light points on the surface of the real piece of wood and ascertaining whether or not physical characteristics of the log are present by evaluating any scatter that may affect those light points, and/or acquiring an X-ray image of the real piece of wood.

5. The method according to claim 1, wherein during the saving step, for each virtual piece of wood, together with the virtual individualising characteristics, information about the dimensions of the virtual piece of wood is also saved in the database.

6. The method according to claim 5, also comprising, after the cutting step, a step of dividing at least one real piece of wood obtained from the cutting step into further real pieces of wood, wherein, during the search step, the real individualising characteristics of the real piece of wood are compared with sub-groups of virtual individualising characteristics saved in the database in order to identify said match, wherein the information about the dimensions of the virtual piece of wood comprises a thickness of the virtual piece of wood, and wherein during the search step the real individualising characteristics of the real piece of wood are compared with sub-groups of virtual individualising characteristics saved in the database with reference to virtual pieces of wood having the same thickness as the real piece of wood and other dimensions greater than or equal to those of the real piece of wood.

7. The method according to claim 1 also comprising, after the step of choosing the cutting pattern, and before the characterising step, the following operating steps:
- a preliminary working step, during which the log is subjected to a preliminary working of cutting or cleaning in accordance with the cutting pattern;
- a checking step, during which the log is measured or analysed after the preliminary working;
- a comparing step, during which the results of the checking step are compared with the cutting pattern in order to verify if the log has been preliminarily worked as foreseen in the cutting pattern; and
- a correcting step for correcting the cutting pattern, to be carried out if the result of the comparing step indicates that the log has been preliminarily worked in a way that is different to what was foreseen, during the correcting step the cutting pattern previously defined being modified in order to adapt it to the real preliminarily worked log.

8. The method according to claim 7, wherein the virtual individualising information defined during the characterising step corresponds to:
- a two-dimensional or three-dimensional distribution of knots on one or more faces of the virtual piece of wood, and/or inside the virtual piece of wood; and/or
- a two-dimensional distribution of grains on one or more faces of the virtual piece of wood; and/or
- a trend of the direction of the fibre of the wood on one or more faces of the virtual piece of wood.

9. The method according to claim 7, wherein the real information acquired during the analysing step corresponds to an arrangement of physical characteristics of the log on an outer surface of the real piece of wood and is obtained either by acquiring an image of an outer surface of the real piece of wood, in colour in the visible and/or infra-red spectra, and/or by projecting one or more light points on the surface of the real piece of wood and ascertaining whether or not physical characteristics of the log are present by evaluating any scatter that may affect those light points, and/or acquiring an X-ray image of the real piece of wood.

10. The method according to claim 1, also comprising, after the cutting step, a step of dividing at least one real piece of wood obtained from the cutting step into further real pieces of wood.

11. The method according to claim 10, wherein, during the search step, the real individualising characteristics of the real piece of wood are compared with sub-groups of virtual individualising characteristics saved in the database in order to identify said match.

12. The method according to claim 10, wherein, before the step of dividing said at least one real piece of wood, there is a step of choosing a secondary cutting pattern which comprises information with reference to a subsequent division of said at least one real piece of wood into further virtual pieces of wood.

13. The method according to claim 12, wherein, before the step of dividing said at least one real piece of wood and after the step of choosing a secondary cutting pattern, there is also a further characterising step, during which, for each further virtual piece of wood intended to be obtained from said at least one real piece of wood, and starting with the tomographic information available, one or more further virtual individualising characteristics are defined which are linked to the distribution and/or size of physical characteristics of the log inside and/or on the surface of the self-same further virtual piece of wood, and wherein during the saving step the virtual individualising characteristics of each further piece of wood are also saved in the database together with information about the identity of the log.

14. The method according to claim 10, wherein the virtual individualising information defined during the characterising step corresponds to:
- a two-dimensional or three-dimensional distribution of knots on one or more faces of the virtual piece of wood, and/or inside the virtual piece of wood; and/or
- a two-dimensional distribution of grains on one or more faces of the virtual piece of wood; and/or
- a trend of the direction of the fibre of the wood on one or more faces of the virtual piece of wood.

15. The method according to claim 10, wherein the real information acquired during the analysing step corresponds to an arrangement of physical characteristics of the log on an outer surface of the real piece of wood and is obtained either by acquiring an image of an outer surface of the real piece of wood, in colour in the visible and/or infra-red spectra, and/or by projecting one or more light points on the surface of the real piece of wood and ascertaining whether or not physical characteristics of the log are present by evaluating any scatter that may affect those light points, and/or acquiring an X-ray image of the real piece of wood.

16. The method according to claim 1, wherein the virtual individualising information defined during the characterising step corresponds to:
- a two-dimensional or three-dimensional distribution of knots on one or more faces of the virtual piece of wood, and/or inside the virtual piece of wood; and/or
- a two-dimensional distribution of grains on one or more faces of the virtual piece of wood; and/or
- a trend of the direction of the fibre of the wood on one or more faces of the virtual piece of wood.

17. The method according to claim 1, wherein the real information acquired during the analysing step corresponds to an arrangement of physical characteristics of the log on an outer surface of the real piece of wood and is obtained either by acquiring an image of an outer surface of the real piece of wood, in colour in the visible and/or infra-red spectra, and/or by projecting one or more light points on the surface of the real piece of wood and ascertaining whether or not physical characteristics of the log are present by evaluating any scatter that may affect those light points, and/or acquiring an X-ray image of the real piece of wood.

18. The method according to claim 1, also comprising:
- a comparison step, during which the real piece of wood obtained is compared with the corresponding virtual piece of wood foreseen in the cutting pattern, and
- a validating step, during which the operation of apparatuses used for implementing the method is validated or not, depending on the result of the comparison step, the operation being validated only when one or more reference characteristics of the real piece of wood deviate from those of the virtual piece of wood by less than a predetermined threshold value.

19. The method according to claim 1, wherein each virtual individualising characteristic is defined by the position of a knot on the surface of the virtual piece of wood and by a predetermined margin of error, calculated depending on the orientation of the knot relative to the surface of the virtual piece of wood, wherein during the analysing step corresponding real individualising characteristics of the real piece of wood are defined which correspond to positions of the knots on the surface of the real piece of wood, and wherein, during the search step, the real individualising characteristics of the real piece of wood are compared with the virtual individualising characteristics saved in the database for each virtual piece of wood taking into account the predetermined margin of error.

20. A method for deciding a cutting pattern to be used for dividing a wooden log into pieces of wood, comprising the following operating steps:
- an initial step of taking a wooden log;
- a scanning step, wherein a tomographic scan of the wooden log is performed;
- a step of choosing a cutting pattern, during which a cutting pattern for the log is calculated or selected, the cutting pattern comprising information with reference both to an outer preliminary working of the log and to a subsequent division of the inner part of the log into pieces of wood;
- a preliminary working step, during which the log is preliminarily worked in accordance with the cutting pattern;
- a checking step, during which the preliminarily worked log is measured or analysed;
- a comparing step, during which the results of the checking step are compared with the chosen cutting pattern in order to verify if the log has been preliminarily worked as foreseen in the cutting pattern; and
- a correcting step for correcting the cutting pattern, to be carried out if the result of the comparing step indicates that the log has been preliminarily worked in a way that is different to what was foreseen, during the correcting step the cutting pattern previously defined being modified in order to adapt it to the real preliminarily worked log.

* * * * *